(12) United States Patent
Beuter et al.

(10) Patent No.: US 11,878,170 B2
(45) Date of Patent: Jan. 23, 2024

(54) APPARATUS AND METHOD FOR CLOSED-LOOP MODEL-BASED ELECTRICAL BRAIN STIMULATION

(71) Applicant: CORSTIM, Montpellier (FR)

(72) Inventors: Anne Beuter, Montpellier (FR); Vitaly Volpert, Villeurbanne (FR)

(73) Assignee: CORSTIM, Montpellier (FR)

( * ) Notice: Subject to any disclaimer, the term of this patent is extended or adjusted under 35 U.S.C. 154(b) by 361 days.

(21) Appl. No.: 17/269,156

(22) PCT Filed: Aug. 14, 2019

(86) PCT No.: PCT/EP2019/071835
§ 371 (c)(1),
(2) Date: Feb. 17, 2021

(87) PCT Pub. No.: WO2020/035536
PCT Pub. Date: Feb. 20, 2020

(65) Prior Publication Data
US 2021/0322773 A1 Oct. 21, 2021

(30) Foreign Application Priority Data
Aug. 17, 2018 (EP) .................................. 18306123

(51) Int. Cl.
*A61N 1/36* (2006.01)
*A61N 1/05* (2006.01)
(52) U.S. Cl.
CPC ....... *A61N 1/36103* (2013.01); *A61N 1/0531* (2013.01); *A61N 1/36139* (2013.01)

(58) Field of Classification Search
CPC .............. A61N 1/36103; A61N 1/0531; A61N 1/36139; A61B 5/4064
See application file for complete search history.

(56) References Cited

U.S. PATENT DOCUMENTS

| 2009/0118787 A1 | 5/2009 | Moffitt |
| 2012/0071947 A1 | 3/2012 | Gupta et al. |
| 2014/0018882 A1 | 1/2014 | Wilke et al. |

FOREIGN PATENT DOCUMENTS

| WO | 2016023126 A1 | 2/2016 |
| WO | 2017223564 A1 | 12/2017 |

OTHER PUBLICATIONS

International Search Report related to Application No. PCT/EP2019/071835 reported on Sep. 27, 2019.
(Continued)

*Primary Examiner* — Paula J Stice
(74) *Attorney, Agent, or Firm* — von Briesen & Roper, s.c.

(57) ABSTRACT

An apparatus for electrical brain stimulation comprises a two dimensional electrode array designed to be implanted at the surface of the cortex of a person, said cortex having neural pre-identified nodes and including healthy cortical tissue and damaged cortical tissue, said damaged cortical tissue having at least one parameter of cortical waves which is different from parameter of healthy cortical tissue, said at least one parameter being one of cortical wave propagation speed, amplitude and frequency, said electrode array including electrodes for emitting stimulation electrical signals in the cortex and measuring electrical cortical waves in the cortex, and said electrode array being designed to cover at least part of said healthy cortical tissue and said damaged cortical tissue.

20 Claims, 5 Drawing Sheets

(56) References Cited

OTHER PUBLICATIONS

Modolo: "Using a virtual cortical module implementing a neural field model to modulate brain rhythms in Parkinson's disease", Frontiers in Neuroscience Jan. 1, 2010 (Jan. 1, 2010), XP055199697, DOI: 10:3389/fnins.2010.00045 pp. 5-7.

Kunze Tim et al: "Transcranial direct current stimulation changes resting state functional connectivity: A large-scale brain network modeling study", NeuroImage, Elsevier, Amsterdam, NL, vol. 140, Feb. 13, 2016 (Feb. 13, 2016), pp. 174-187, XP029723964, ISSN 1053-8119, D0I:10.1016/J.NEUROIMAGE.2016.02.015 abstract.

APPARATUS AND METHOD FOR CLOSED-LOOP MODEL-BASED ELECTRICAL BRAIN STIMULATION

CROSS-REFERENCE TO RELATED APPLICATION

This Application is a 35 USC § 371 US National Stage filing of International Application No. PCT/EP2019/071376 filed on Aug. 8, 2019 and claims priority under the Paris Convention to French Patent Application No. 18 57439 filed on Aug. 10, 2018.

FIELD OF THE DISCLOSURE

The instant description relates to an apparatus and method suitable for electrical brain stimulation, providing an adaptive stimulation signal in space and time in order to modulate the propagation of electrical waves of cortical activity.

BACKGROUND OF THE DISCLOSURE

The brain can be stimulated by way of either one of electrical, magnetic and optogenetic means in order to treat various neurological conditions. The stimulation of brain can be invasive, implying the need to open the skull and implant some stimulation means directly on and/or inside the brain tissue. The stimulation of brain can be non-invasive, leaving the skull intact and applying the stimuli from outside thereof.

WO2017/223564 for example describes systems, methods and devices for promoting recovery from a stroke which induced loss of motor function in a subject. The system includes (an) electrode(s), and an operations system in electrical communication with (an) electrode(s), wherein the electrode(s) is/are constructed and arranged to apply current across the brain of the subject and to record low frequency oscillations (LFO) from a perilesional region of the subject. A recording electrode can be placed in electrical communication in a perilesional region of the subject; a stimulation electrode can be placed in electrical communication with the brain of the subject; low frequency oscillations (LFO) from the perilesional region of the subject are recorded; and current stimulation is delivered to the brain of the subject.

In the above example of prior art, focus is made on treatment of loss of motor functions after stroke. This is why low frequency oscillations are detected, since the low frequency oscillations are considered to be associated to motor functions in an individual. Here in this prior art example the LFO recorded at the perilesional site is used to determine stimulation parameters of alternating current stimulation. Then, wave form and frequency of the alternating current stimulation is calculated to match the recorded LFO. Discrete pulses of current stimulation are then applied to perilesional areas to potentiate motor task related LFOs.

Also, in the above prior art the LFO stimulation occurs at one electrode or, possibly, simultaneously at several electrodes with the same signal at each electrode, without considering spatial propagation (travelling) of waves. "Wave" in the above cited prior art example concerns the form of time oscillations but it does not concern spatial propagation. Nevertheless, recent experimental and clinical data suggest that the information in the brain cortex propagates in space between cortical nodes in the form of travelling waves. The speed, the amplitude, and the form (frequency) of travelling waves between different cortical nodes have a primary importance for the normal brain functioning.

In the case of cortical damage, all these vast signalling pathways cannot be stimulated by a single signal with LFO.

The instant disclosure has notably for object to improve the existing invasive and non-invasive brain stimulation apparatuses and methods by stimulation of spatially propagating travelling waves between pairs of cortical nodes participating in language function or in the other brain functions.

SUMMARY OF THE DISCLOSURE

In contrast to the above cited prior art, the below disclosure has been motivated in particular by finding solution to post-stroke treatment of aphasia consisting in stimulation of spatially propagating (travelling) waves between pairs of cortical nodes participating in language function. Nevertheless, other stroke related disorders can be treated with the very same method and apparatus and it has also been confirmed that other than stroke-related brain dysfunctions can be treated as well. To this aim, the present disclosure provides an apparatus for electrical brain stimulation comprising:

a two dimensional electrode array designed to be implanted at the surface of the cortex of a person, said cortex having pre-identified crucial neural nodes and including healthy cortical tissue and damaged and/or partially damaged cortical tissue, said damaged and/or partially damaged cortical tissue having at least one parameter of cortical waves which is different from parameter of healthy cortical tissue, said at least one parameter being one of cortical wave propagation speed, amplitude and frequency, said electrode array including electrodes for emitting stimulation electrical signals in the cortex and measuring electrical cortical waves in the cortex, and said electrode array being designed to cover at least part of said healthy cortical tissue and said damaged and/or partially damaged cortical tissue;

a processor communicating with the electrodes and configured to:
  based on the measured signals, evaluate said at least one parameter of cortical waves between at least a first electrode and at least a second electrode corresponding respectively to a first pre-identified crucial neural node and a second pre-identified crucial neural node in the cortex, said first pre-identified crucial node and second pre-identified crucial node being situated such that a rectilinear line joining the first pre-identified crucial node and the second pre-identified crucial node crosses said damaged and/or partially damaged cortical tissue;
  compute in real time, stimulation signals required to maintain said at least one parameter of cortical waves in a predetermined range between said first electrode and said second electrode and apply said computed stimulation signals to the electrodes.

Especially, compared to the prior art cited in the background section, the present disclosure relies on identifying at least two crucial neural nodes (based on structural and functional relations) and applying external stimulation signal between these pre-identified crucial nodes, thereby restoring functions of the brain. In the above prior art, wave form and frequency of the alternating current stimulation is calculated to match the recorded LFO. In contrast, the present disclosure does not intent to find match between applied alternating current and detected LFOs (nor other oscillations). Instead, the claimed subject matter has to purpose of restoring a match between brain waves in the healthy and damaged cortical tissue. This is done by restoring match between parameters of the brain waves of the healthy and damaged cortical tissue.

The features of the above defined apparatus respectively comprise means for measuring electrical cortical waves in the cortex, means for evaluating at least one parameters of cortical waves based on the measured signals, and means for computing and applying in real time the stimulation signals required said at least one parameter of cortical waves in a predetermined range. This sequence of steps creates a closed-loop, such that the apparatus can continuously receive input from the electrodes and react by appropriate modifications of the external stimulation signal.

With these features, the claimed apparatus acts to restore the parameter of cortical waves in the case of reduced connectivity and excitability among individual nodes of the cortical tissue. Two cases may occur. First, the electrical stimulation may increase the connectivity of the damaged and/or partially damaged cortical tissue, in which case the effect of external stimulation may last beyond the stimulation (i.e. after the stimulation is stopped), thereby effectively restoring brain functionality. Second, the external stimulation signal may modify excitability, leading at least to temporal stimulation and improvement of brain function, thereby effectively assisting to restore some brain function, but however not leading to complete recovery of the brain functionality.

With the claimed apparatus, it is possible to induce propagation of waves of electric potential in the cortical tissue thereby generating electrical activity across the cortex at different speeds and progressing in different directions, such as straight, spiral and other possible directions.

Relevance of pre-identifying crucial neural nodes prior to application of the external stimulation lies in the fact that it allows to apply the external stimulation signal to the most appropriate location on the cortex. This enhances efficiency of the apparatus. Also, locating electrodes on pre-determined crucial nodes allows to apply the external stimulation signal having spatial dependency, i.e. the external stimulation signal is determined according to its position in space (location on the cortex).

The claimed apparatus enables to sustain wave propagation in the cortex and contributes to cortical network reactivation.

The closed-loop approach has the advantage that the signal reaching the brain area is programmed to adapt to coexisting brain activity with the consequence that the external stimulation signal does not have to be regularly adjusted manually by the clinician and the external stimulation can be tailored to the individual's needs.

Further, the arrays of electrodes can provide information about speed of wave propagation in the diseased (damaged or partially damaged) cortical tissue.

In some embodiments of the above defined apparatus, one might also use one or more of the following features:

said predetermined range corresponds to values of said at least one parameter of cortical waves in the healthy cortical tissue;
said processor is configured to compute said stimulation signals for the first electrode and second electrode and apply said computed stimulation signals to the first electrode and the second electrode;
said at least one parameter of cortical waves is maintained between said first electrode and second electrode via at least one third electrode, and wherein said processor is configured to (i) based on the measured signals from said first electrode, second electrode and at least one third electrode, evaluate said at least one parameter of cortical waves between pairs of adjacent electrodes among said first electrode, second electrode and at least one third electrode; (ii) compute said stimulation signals for said first electrode, second electrode and at least one third electrode, and apply said computed stimulation signals to said first electrode, second electrode and at least one third electrode;

said at least one third electrode includes a plurality of third electrodes;
said plurality of third electrodes form a path designed to be situated at least in part in the damaged and/or partially damaged cortical tissue;
said plurality of third electrodes form a path designed to be situated in the healthy cortical tissue;
said path is designed to be situated at the edge of the damaged and/or partially damaged cortical tissue;
the apparatus is configured to simultaneously stimulate selected pair of electrodes associated with specific pair of pre-identified crucial neural nodes.
said processor is configured to compute said stimulation signals by using a mathematical model of propagation of cortical waves;
the processor is configured to apply the mathematical model of propagation of cortical waves, such that each stimulation signal is determined by a stimulation function $I(x,t)$, where the stimulation function is a function of space coordinates (this allows to apply external stimulation signal in each electrode of the electrode array differently, such that the spatial propagation of wave—travelling—in the brain cortex is properly respected during treatment);
the processor is configured to operate the electrode array such that each electrode in the electrode array applies external stimulation signal (determined by value of stimulation function) dependent on electrode's location on the brain cortex (by applying different stimulation signal in each electrode of the electrode array the spatial propagation of brain waves is respected and the efficiency of the apparatus may be improved; of course this embodiment also includes case where a number of electrodes applies the same external stimulation and one or more other electrodes apply different external stimulation signal; the most appropriate value of external stimulation can be selected for each electrode individually);
each stimulation signal is determined by a stimulation function $I(x,t)$, and the computer processor is configured to calculate numerically the stimulation function $I(x,t)$ applied to each electrode at the damaged and/or partially damaged cortical tissue and the healthy tissue by numerically solving the equation:

$$I(x,t)=g(K-u)(H(W_a^{(1)}(u))-H(W_a^{(2)}(u)))-g(u)(H(W_i^{(1)}(u))-H(W_i^{(2)}(u)))$$

where K is a total neuron density, K−u is a density of not activated neurons, $W_a$ is an intensity of the activating signal, $W_i$ is an intensity of the inactivating signal, superscript (1) corresponds to the healthy tissue and superscript (2) to the damaged or partially damaged tissue, $g(u)$ and $H(W)$ are growing functions of said intensity of activating signal, $(K-u)W_a$ represents a rate of neuron activation and $uW_i$ represents a rate of neuron inactivation, the processor is configured to apply external stimulation signal determined by the stimulation function I(x,t) having the lowest value of the total stimulation $\int_0^T \int_\Omega I^2(x,t)dxdt$ the processor is configured to apply external stimulation signal determined by the stimulation function I(x,t) having the lowest value of maximal stimulation=max I(x,t);

the processor is configured to determine the value of external stimulation signal determined by the stimulation function I(x,t), such that the process determines wave speed in the cortical tissue according to the formula $$c = \left(1 - \frac{2}{\sigma\gamma} + \frac{2I}{b\gamma}\right)$$

where σ characterizes cortical tissue excitability and γ characterizes cortical tissue connectivity;

the processor is configured to determine whether the condition of

σγ>2 is satisfied in the cortical tissue, where σ is a parameter characterizing cortical tissue excitability of healthy cortical tissue and γ is a parameter indicating cortical tissue connectivity.

Another object of the present description is a method for electrical brain stimulation comprising the steps of:

providing a two-dimensional electrode array including electrodes;

implanting the two-dimensional electrode array at the surface of the cortex of a person, said cortex having pre-identified crucial neural nodes and including healthy cortical tissue and damaged and/or partially damaged cortical tissue, said damaged and/or partially damaged cortical tissue having at least one parameter of cortical waves which is different from parameter of a healthy cortical tissue, said at least one parameter being one of cortical wave propagation speed, amplitude and frequency;

emitting by the electrodes a stimulation electrical signals in the cortex and measuring electrical cortical waves in the cortex;

covering by the electrode array at least part of the healthy cortical tissue and the damaged and/or partially damaged cortical tissue;

based on the measured signals, evaluating said at least one parameter of cortical waves between at least a first electrode and at least a second electrode corresponding respectively to a first pre-identified crucial neural node and a second pre-identified crucial neural node in the cortex, said first pre-identified crucial neural node and second pre-identified crucial neural node being situated such that a rectilinear line joining the first pre-identified crucial neural node and the second pre-identified crucial neural node crosses said damaged and/or partially damaged cortical tissue;

computing in real time, stimulation signals required to maintain said at least one parameter of cortical waves in a predetermined range between said first electrode and said second electrode and applying said computed stimulation signals to the electrodes In some embodiments of the above defined method, one might also use one or more of the following additional steps:

the method is used to treat post-stroke aphasia and/or other brain disorders in which traveling waves parameters need to be restored the method is used along with active participation of the patient during the external stimulation the method is used to treat post-stroke aphasia the applied computed stimulation signal are not applied to the electrode continuously, more particularly the applied computed stimulation signal is applied to the electrodes at discrete moments in time (such feature is designed for optimizing battery use and provide a more appropriate patient specific treatment, since the external stimulation can be reinjected only when necessary, for example only when the match between parameters of the brain waves of the healthy cortical tissue and the parameters of the brain waves in the damaged cortical tissue becomes larger than a predetermined tolerance).

Other characteristics and advantages will readily appear from the following description of one embodiment, provided as a non-limitative example, and of the accompanying drawings.

BRIEF DESCRIPTION OF THE DRAWINGS

On the different Figures, the same reference signs designate like or similar elements.

DETAILED DESCRIPTION OF THE DISCLOSURE

One of the applications of the disclosure lies in treating aphasia, which is an impairment of language processing (often resulting from stroke). Long term aphasia is increasingly common among the population and since the post-stroke language disorders are closely related to poor quality of life, there is an increased need for providing suitable method and apparatuses for treatment and possible recovery of the brain tissue. Even when the brain functions cannot be re-established completely, partial recovery of brain tissue is often possible and/or the patient can be assisted by the apparatus to maintain, improve or gradually restore the brain function.

Even though the focus is made on stroke disorders in the brain, it has been studied and concluded that the below described method and apparatus can be equally used to address other brain disorders as well. Comparable results with those presented below are obtained for other brain disorders. Generally, the disclosure could relate to any neurological disorder of the nervous system causing structural, biochemical, and/or electrical abnormalities in the brain, spinal cord or other nerves.

Generally, there is increasing pressure to find new therapeutic options to help stroke patients recover normal functions or at least to optimize their residual functions when all other options have been exhausted. During early recovery phase following stroke therapies such as neuroprotection, blood flow restoration, pharmacotherapy, and intensive training may improve symptoms significantly. Still yet, estimates conclude that post-stroke impairments persist in up to 40% of patients for more than a year.

Recovery of the damaged brain tissue can occur spontaneously but can be amplified and accelerated by the use of non-invasive and/or invasive brain stimulation techniques. During the very late stage of recovery improvements appear to reach a plateau. The problem solved thus lies in finding how brain stimulation techniques could enhance remaining cortical excitability in the affected hemisphere. Solutions to this problem are provided by the technique of the present method and apparatus.

Generally, the method and apparatus presented in the current application introduces a mathematical model adapted to determine external electrical stimulation signal adjusted in such a way that wave speed or other parameters of the brain waves can be reconstructed. Simultaneously, with the treatment present in this application, a patient can undertake any standard rehabilitation therapy available, in order to enhance the effect of the electrical stimulation. The rehabilitation therapy may involve activities related to language such as exercising lexical memory or phonological processing.

In comparison with existing non-invasive brain stimulation and recovery techniques the present disclosure is advantageous, since it does not have the usual drawbacks of the non-invasive techniques. Non-invasive techniques have limited spatial and temporal resolution. As far as the existing deep brain stimulation techniques are concerned, these techniques are also associated with certain drawbacks. Especially, deep brain stimulation has limitations such as presence of side effects or limited battery life necessitating surgery for its replacement. Finally, it should be noted that the current optogenetic techniques are not yet ready for human cortical stimulation.

Figure 1:
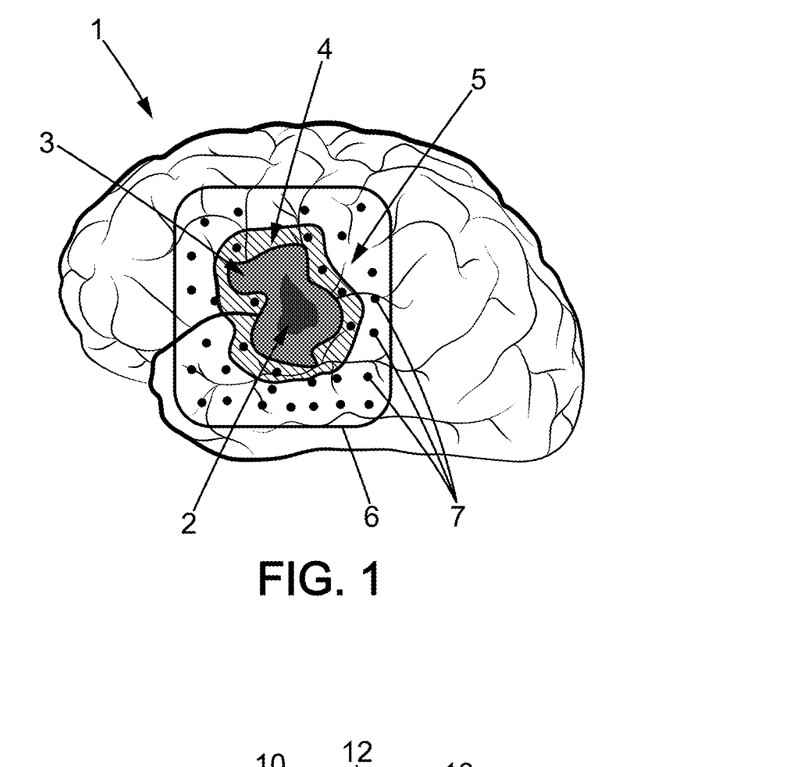
FIG. 1 illustrates a brain showing areas of healthy cortical tissue, damaged and partially damaged cortical tissue.

With reference to FIG. 1, following a stroke, the tissue in the brain 1 is affected in some areas. Generally, the areas can be divided into four types. The central infarct area 2 containing dead cells is called umbra 2 and this area contains damaged neural cells. In the present application, umbra is also referred to as damaged cortical tissue 2. Around the umbra 2, there is ischemic tissue called penumbra 3, this area contains partially damaged neural cells and may recover after the stroke. In penumbra 3 brain neural networks are fragmented and partly deactivated. In the present application, penumbra 3 is also referred to as partially damaged cortical tissue. Around the penumbra 3, there could optionally be identified so called perilesional area 4, which could have partially retained its functions but which had also usually been affected by the stroke (having effect for example on its structure). For the purposes of this disclosure, perilesional area will also be referred to as partially damaged cortical tissue, unless specific difference between the penumbra 3 and the perilesional area will be specifically pointed out in the text. Finally, around the neural cortical area of the brain affected by the stroke there is the area which remains fully structurally intact and entirely functional. This area either referred to as viable cortex 5 or as healthy cortical tissue 5.

Concerning the partially damaged cortical tissue, it is considered that wave speed of propagation of electrical signal between neurons in penumbra 3 and in perilesional area 4 is affected by the stroke. Generally, a wave speed can be determined by tissue excitability and connectivity, which are parameters associated with applied model for brain waves. How these parameters can be defined in terms of concrete physical and mathematical terms will be explained later below. Post-stroke tissue damage in penumbra or perilesional area 4 creates hypoconnectivity and decreases the speed of wave propagation. According to the present disclosure, wave speed or other parameters of the waves can be restored through external electrical stimulation.

The regions of the brain 1 relevant for the present disclosure are the area of cerebral cortex. Cortex is the outer covering of grey matter over brain's hemispheres. The layer or cortex is typically 2-3 mm thick. Different areas of cortex receive various sensory inputs such as vision, hearing and similar, or could be directly involved in functions such as production of limb or eye movements. Cortical areas may further be related to more complex functions such as memory, language, abstraction, creativity, emotion and similar.

Studies of brain structure and brain function have revealed the existence of complex and multiple brain networks. In the present disclosure, pre-identified crucial nodes refer to nodes connecting different networks by virtue of their numerous and diverse connections (i.e., connector nodes). Crucial nodes are located differently in each person. For that reason, the model according to which the external stimulation is applied is individualized to characteristics of specific subject and to every person's therapeutic needs. Stimulated crucial neural nodes are pre-identified via structural and functional connectivity measures. The external electrical stimulation method of this application and the associated apparatus can be used along with active participation of the patient during the external stimulation or it can be used while the subject is at rest.

Considering the specific application of treating aphasia and adjustments made in order to address complex human brain structure, the present disclosure is specifically adapted for use with human patients. Both the method and the apparatus are thus applied to humans only.

In the present disclosure, the method and apparatus are based on use of a two dimensional electrode array 6 adapted to be implanted at the surface of the cortex, as known in the art. The electrode array 6 includes electrodes 7 for emitting stimulation electrical signals in the cortex and measuring electrical cortical waves in the cortex. Further, the position of at least some of said electrodes 7 correspond respectively to pre-identified crucial neural nodes in the cortex. This means that the electrodes 7 are positioned at selected areas of brain tissue with regard to brain structure and functionality, as well as with regard to which part of the brain 1 is damaged and/or partially damaged. The electrode array 6 may be integrated in a flexible material suitable for closely covering the surface of the cortex.

Figure 2:
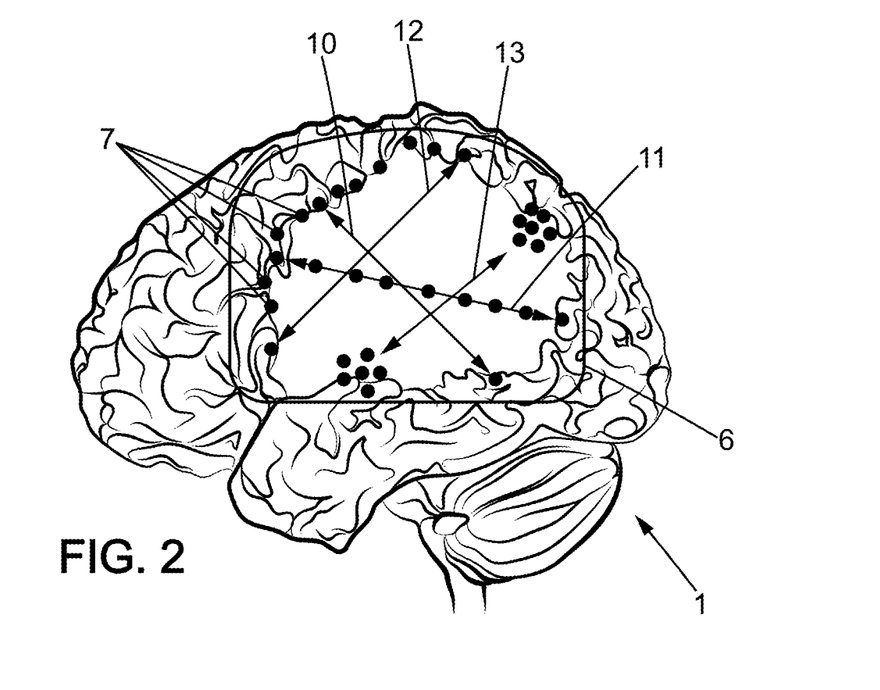
FIG. 2 illustrates different ways to reconnect pre-identified crucial neural nodes according to the recent disclosure.

Both FIG. 1 and FIG. 2 illustrate electrodes 7 as dots. Every single dot represents one electrode 7. The electrodes can be provided in any desired number and any desired density on the surface of the brain tissue. Schematic representation of electrodes 7 on the drawings is not intended as limitation. Rather, the drawings merely illustrate such a number of electrodes required for easy understanding of the principles of the disclosed method and apparatus.

Figure 7:
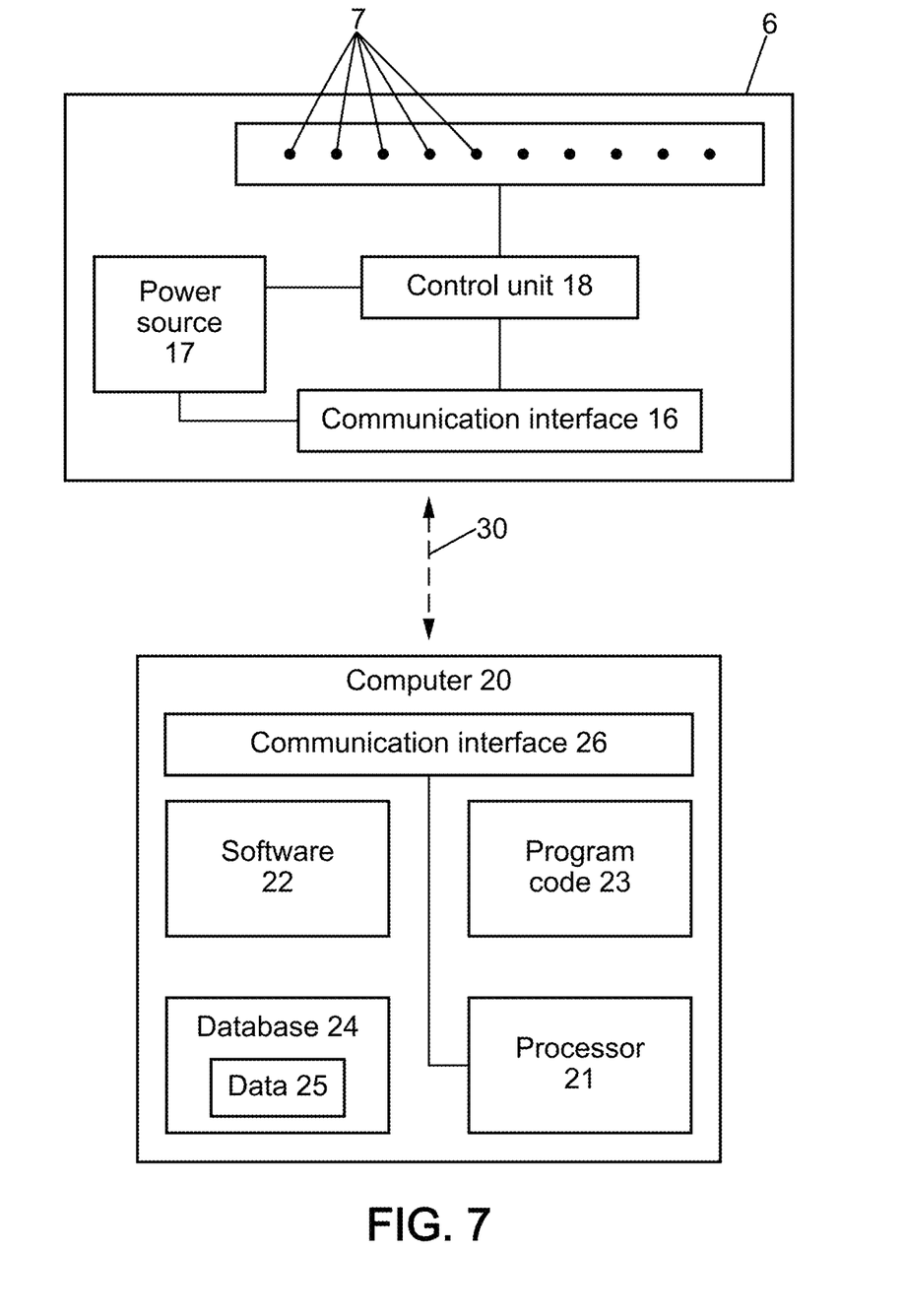
FIG. 7 is a schematic illustration of the components of the claimed apparatus.

Referring to FIG. 7, the apparatus for performing the electrical brain stimulation of the present disclosure may include a computer 20, where the computer includes database 24 comprising data 25, where the data 25 are related to models of the brain tissue and include relevant input parameters which are used in the equations below. Relevant input parameters could be for example neuron density K, excitation speed q, neuron connection strength $\varphi_0$ or neuron connection distance a. The computer 20 may further include a program code 23 implementing all relevant mathematical equations. The computer 20 may further include a software 22, which could be in a form a user interface or and/or an application allowing an operator to select and/or modify input parameters, or to select/modify relevant equations to be used for the computations.

The array 6 of electrodes may include a control unit 18 driving the electrodes 7 individually and receiving sensed signals from said electrodes 7. The control unit 18 may be located near the electrodes 7 or at another appropriate location on the patient. The control unit 18 is powered by a power source 17, such as battery or other suitable power source.

Both the electrode array 6 and the computer 20 include a communication interface 16, 26. A communication interface 16 is associated with the electrode array 6 and a communication interface 26 is associated with the computer 20, enabling communication between processor 21 and control unit 18. The communication interfaces 16, 26 allow for transfer of signals, data and instructions about the form and intensity of the stimulation signal to be applied by the electrodes 7. The communication interfaces 16, 26 may communicate via a communication link 30 which could be wired or wireless communication or a combination thereof.

FIG. 2 illustrates a brain 1 including a damaged and/or partially damaged cortical tissue (continuous white area of FIG. 2). FIG. 2 shows electrodes 7 and electrodes paths relevant for successful restoration of the wave speed and/or other wave parameters.

FIG. 2 further illustrates that an exemplary connection 10 between a pair of neural nodes might have been lost due to stroke or other reasons in the brain, since the connection 10 leads through the damaged and/or partially damaged area, but communication between the nodes is recreated by stimulation of the electrodes 7 which correspond to these neural nodes as explained below. As shown, the connection path 10 involves only communication between a pair of neural nodes (represented by two stimulation electrodes 7). Such communication is the most direct and could be successful in recreating some of the brain functions especially when the damaged brain area is not large.

Various other stimulation configurations are contemplated in the present disclosure.

For example, the stimulation path 11 of FIG. 2 between two nodes leads through the damaged cortical area through a number of intermediate electrodes 7. The stimulation path 11 may lead to wave propagation reconstruction between its endpoints by applying stimulation signals to all electrodes 7 of path 11 and sensing cortical waves by said electrodes 7, in order to restore at least one cortical wave parameter as explained below. In some cases, the stimulation route 11 may lead to restoration of brain functions only temporarily, since the damaged brain tissue does not allow to restore all functions completely. In certain cases therefore, the stimulation route 11 may be used for the purposes of neural assistance, i.e. to use the electrodes 7 permanently in order to substitute for the normal brain functions.

The advantage of stimulation path 11 is that the connection between two endpoints (neural nodes represented by two endpoint-electrodes 7) can be selected through a specific route according to every person's needs. The stimulation signal can thus be designed with a concrete purpose according to the special needs of each and every individual. On the practical level, the electrode array 6 may contain any appropriate density of electrodes 7. The number of electrodes 7 in the array 6 may be selected such that each single neural node is covered by an associated electrode 7. However, during application of the external stimulation signal only some of the electrodes can be activated (thus generating the external electrical signal), for example only those electrodes 7 may be activated which are positioned along a specific path 11. However, if another path is selected other electrodes 7 representing another path may be activated instead.

Alternatively, to the above approach, the carrier (such as a flexible material for closely covering the surface of the cortex) of the electrode array 6 may only contain those electrode 7 which represent the path 11. Therefore, the brain is not covered with electrodes 7 which are not used.

The stimulation path 12 may be used similarly as stimulation path 11 but creates a relay route around the damaged and/or partially damaged cortical tissue, thus enabling to permanently restore communication between its endpoints at least in some cases.

Once two crucial nodes are reconnected via stimulation, a pairwise neural node communication in the cortex becomes possible.

The stimulation route 13 illustrates paired communication between two groups of electrodes 7, each group corresponding to one neural node in the cortex.

The local density distribution u of activated neurons at point x and time t in the healthy cortical tissue of the cortex can be expressed as:

$$\frac{\partial u}{\partial t} = g(K-u)H(W_a^{(1)}(u)) - g(u)H(W_i^{(1)}(u)) \quad (1)$$

Furthermore, $g(K-u)H(W_a^{(1)})$ represents the rate of neuron activation and $g(u)H(W_i^{(1)})$ represents the rate of neuron inactivation. Here, K is total neuron density, K-u is density of not activated neurons, g and H are positive growing functions, in particular, these functions can be sigmoid functions. $W_a^{(1)}(u)$ is the intensity of activating signal and $W_i^{(1)}(u)$ is the intensity of inactivating signal in the healthy cortical tissue. Both $W_a^{(1)}(u)$ and $W_i^{(1)}(u)$ depend on the local density distribution of activated neurons in space and in time. More particularly, $W_a^{(1)}(u)$ and $W_i^{(1)}(u)$ can be expressed (without using the superscript (1)) as:

$$W_a(x,t) = \int_\Omega \varphi_a(|x-y|)S_a\left(u\left(y, t - \frac{|x-y|}{q_a}\right)\right)dy, \text{ and} \quad (2)$$

$$W_i(x,t) = \int_\Omega \varphi_i(|x-y|)S_i\left(u\left(y, t - \frac{|x-y|}{q_i}\right)\right)dy \quad (3)$$

Here $\varphi_a$ and $\varphi_i$ are connectivity functions, $S_a$ and $S_i$ are the neuron response functions, $q_a$ and $q_i$ are the speeds of signal propagation in neuron axons (excitation speeds). With regard to equations (1), (2) and (3) various particular and mathematically limiting cases can be considered where the functions g and H are linear, or where the neuron connectivity functions $\varphi_a$ and $\varphi_i$ have narrow distributions, or where the excitation speeds (speeds of signal propagation) $q_a$ and $q_i$ are large, or where the neuron response functions $S_a$ and $S_i$ (which will be described in more detail below) are approximated by sigmoid or step-wise constant functions, or where the integral terms are expanded leading to the appearance of the diffusion term in the equation. A system of equations similar to equation (1) can be considered for different neuron subpopulations.

Figure 3:
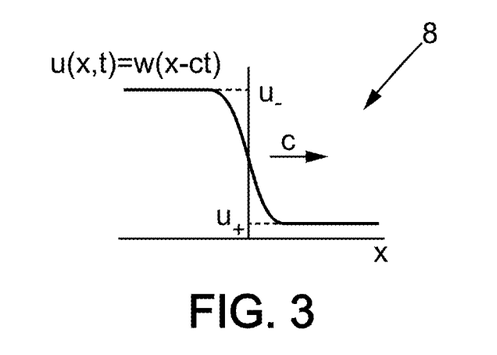
FIG. 3 is an illustration of propagation of a monotonic wave with a wave speed c.
Figure 4:
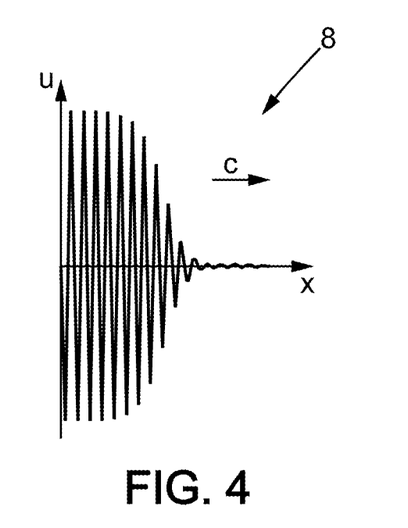
FIG. 4 is an illustration of propagation of an oscillating wave with an average wave speed c.
Figure 5:
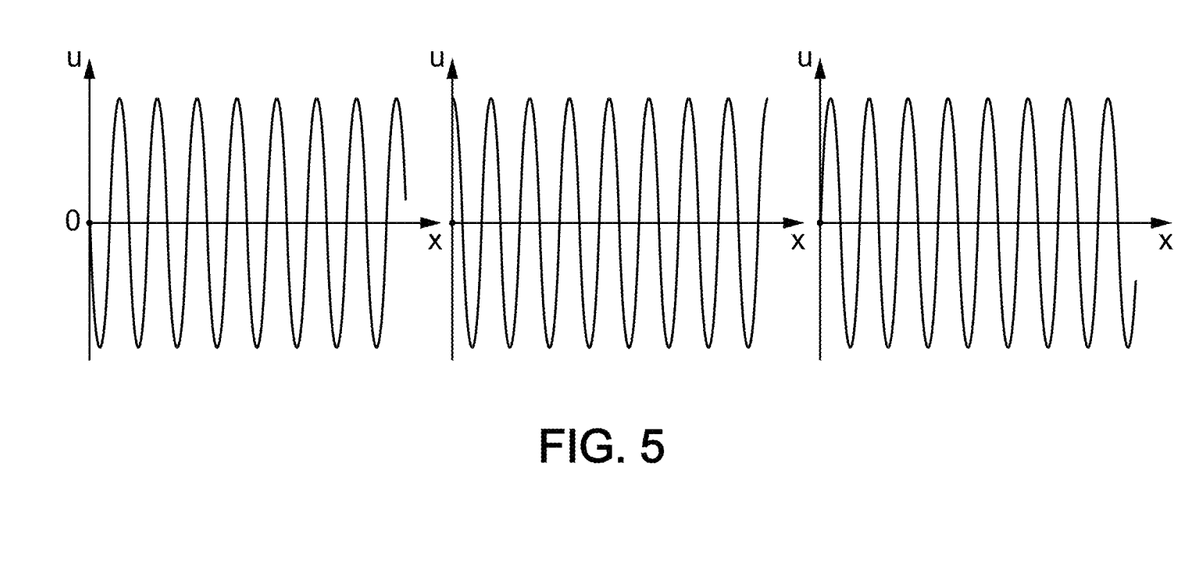
FIG. 5 shows periodic waves propagation in numerical simulations similar to those registered experimentally in electrode arrays (as shown on FIG. 6)
Figure 6:
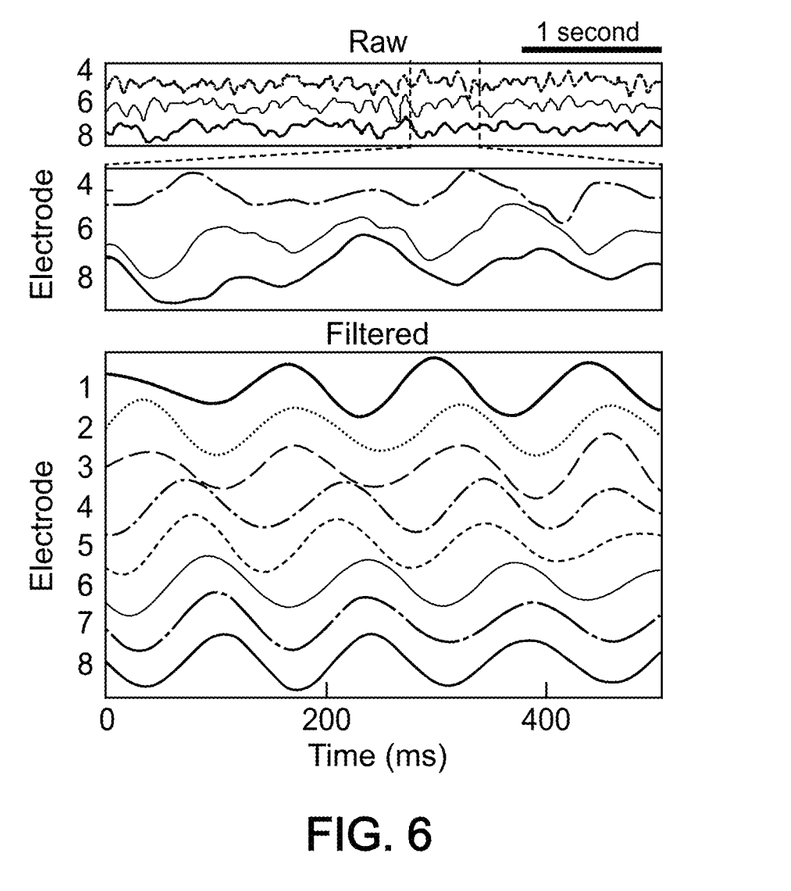
FIG. 6 shows experimentally registered periodic waves registered in electrode arrays (the illustration is taken from a scientific publication of Zhang H, Watrous A J, Patel A, & Jacobs J., *Theta and alpha oscillations are traveling waves in the human neocortex*, (2018) Neuron, 98, 1-13 June 27)

The mathematical model presented in the current disclosure describes propagation of various wave types (waves generally denoted by a reference number 8), including monotonic waves and oscillating waves (see FIG. 3 illustrating a monotonous wave and see FIG. 4 illustrating an oscillating wave). The model describes high frequency oscillations with low frequency amplitude modulations in the form of periodic waves (FIG. 5) resembling those registered experimentally in the electrode arrays (see experimental results illustrated on FIG. 6).

The local density v of activate neurons at point x and time t in the damaged or partially damaged cortical tissue can be expressed as:

$$\frac{\partial v}{\partial t} = g(K-v)H(W_a^{(2)}(v)) - g(v)H(W_i^{(2)}(v)) + I(x,t)$$

Here $W_a^{(2)}(v)$ is the intensity of activating signal and $W_i^{(2)}(v)$ is the intensity of inactivating signal in the damaged cortical tissue. Further, the value of external stimulation signal can be expressed as given by a stimulation function I(x,t).

The computer processor may be configured to numerically calculate the stimulation function I(x,t) applied to each electrode 7 at the damaged cortical tissue 3,4 and healthy cortical tissue 5:

$$I(x,t) = g(K-u)(H(W_a^{(1)}(u)) - H(W_a^{(2)}(u))) - g(u)(H(W_i^{(1)}(u)) - H(W_i^{(2)}(u)))$$

in order to restore the total properties of wave propagation between the neural nodes of the damaged cortex to the corresponding properties in the healthy cortical tissue, including wave speed, frequency, and amplitude.

The connectivity function φ used in equations (2) and (3) represents the physical parameter of connectivity between neural nodes in the cortical tissue in the brain. The connectivity function φ can be defined for example as a simple step-wise constant function:

$$\varphi(x) = \begin{cases} \varphi_0 & \text{for } |x||x|x \le a \\ 0 & \text{for } |x| > a \end{cases}$$

where $\varphi_0$ is a parameter which characterizes connection strengths between neural nodes and where a is a parameter which characterizes neuron connection distance, i.e. a distance across which the connection between two neurons can take place. The step-wise function is a simple and generic approximation of nonlocal interaction which occurs between neural nodes. Other model functions can be selected for the connectivity function φ instead of the step-wise constant function, for example a decreasing exponential function $\varphi = \varphi_0 \exp(-r|x|)$, with $\varphi_0$ and r having similar meaning as $\varphi_0$ and a above. The connectivity function W can also be a sum of two or more exponential functions, where these function will also be based on parameters characterizing connection strength and connection distance. Parameters like $\varphi_0$, a, or r mentioned above can be based experimental data indicative of range of neural fibers and/or strength of inhibitory/excitatory connections. Depending on the model, the connectivity function can be a one dimensional or multidimensional function, such as two-dimensional or three-dimensional.

Another characteristic of the brain tissue is the excitability of the nodes. Excitability is essentially equivalent to capability of neural nodes to transmit electrical signal. The electrical signal travels through cortical tissue in the form of electrical waves. The electrical waves are characterized by their speed c that can be determined by the approximate formula:

$$c = \left(1 - \frac{2}{\sigma\gamma} + \frac{2I}{b\gamma}\right)$$

Concerning the process of application of the external stimulation, the processor 21 can be configured to apply external stimulation signal determined by the stimulation function I(x,t) having the lowest value of the total stimulation=$\int_0^T \int_\Omega I^2(x,t)dxdt$ or the lowest value of the maximal stimulation=max I(x,t). This is an optimal control problem giving the opportunity to reconstruct the solution u(x,t) not for all values of x, but only in one or several points $x_i$, i.e. for one or several electrodes associated with locations $x_i$.

The processor 21 may further be configured to determine the value of external stimulation signal (defined by the stimulation function I(x,t)) in order to restore the wave speed determined by the formula $$c = \left(1 - \frac{2}{\sigma\gamma} + \frac{2I}{b\gamma}\right)$$

in the particular case where the neuron activation response function $S_a$ is approximated by a step function, under the condition σγ>2. Here σ characterizes tissue excitability and γ characterizes tissue connectivity. If the condition is satisfied it is ensured that the mathematical model outputs positive values of the wave speed, which is the necessary condition for the model to give realistic results.

σ is the parameter characterizing cortical tissue excitability of healthy cortical tissue and γ is a parameter indicating cortical tissue connectivity. The positive value of wave speed can thus be only achieved if the product of tissue excitability and connectivity is sufficiently large. It is also implied by the above expressions that the excitability and connectivity of the cortical tissue increases the wave speed of electrical waves propagating trough the cortical tissue as signal.

The invention claimed is:

1. An apparatus for electrical brain stimulation comprising:
   a plurality of electrodes for generating electrical activity in a cortex of a person, the cortex having pre-identified crucial neural nodes associated with a selected brain function and including healthy cortical tissue and damaged and/or partially damaged cortical tissue, wherein the damaged cortical tissue includes damaged neural cells and the partially damaged cortical tissue includes partially damaged neural cells,
   the healthy, the damaged and/or partially damaged cortical tissue each having at least one parameter of cortical waves, wherein a value of the at least one parameter the damaged and/or partial damaged cortical tissue is different from a value of the at least one parameter of the healthy cortical tissue, the at least one parameter being one of cortical wave propagation speed, amplitude and frequency,
the plurality of electrodes including electrodes for emitting stimulation electrical signals into the cortex and measuring electrical cortical waves,
and the plurality of electrodes being designed to emit stimulation electrical signals in at least part of the healthy cortical tissue and the damaged and/or partially damaged cortical tissue, wherein at crucial neural nodes;
a processor communicating with the plurality of electrodes and configured to:
evaluate the at least one parameter of cortical waves between at least a first electrode and at least a second electrode corresponding respectively to a first pre-identified crucial neural node and a second pre-identified crucial neural node in the cortex based on the electrical cortical waves measured by the first electrode and the second electrode between the first pre-identified crucial neural node and the second pre-identified crucial neural node, the first pre-identified crucial node and second pre-identified crucial node being situated such that a rectilinear line joining the first pre-identified crucial node and the second pre-identified crucial node crosses the damaged and/or partially damaged cortical tissue;
compute in real time, stimulation signals required to maintain the at least one parameter of cortical waves in a predetermined range between the first electrode and the second electrode and apply the computed stimulation signals to the plurality of electrodes.

2. The apparatus according to claim 1, wherein the predetermined range corresponds to values of the at least one parameter of cortical waves in the healthy cortical tissue.

3. The apparatus according to claim 1, wherein the processor is configured to compute the stimulation signals for the first electrode and second electrode and apply the computed stimulation signals to the first electrode and the second electrode.

4. The apparatus according to claim 1, wherein the at least one parameter of cortical waves is maintained between the first electrode and second electrode via at least one third electrode,
and wherein the processor is configured to:
based on the measured signals from the first electrode, second electrode and at least one third electrode, evaluate the at least one parameter of cortical waves between pairs of adjacent electrodes among the first electrode, second electrode and at least one third electrode;
compute the stimulation signals for the first electrode, second electrode and at least one third electrode, and apply the computed stimulation signals to the first electrode, second electrode and at least one third electrode.

5. The apparatus according to claim 4, wherein the at least one third electrode includes a plurality of third electrodes, and wherein optionally the plurality of third electrodes form a path designed to emit stimulation electrical signals at least in part in the damaged and/or partially damaged cortical tissue.

6. The apparatus according to claim 5, wherein the plurality of third electrodes form a path designed in emit stimulation electrical signals in the healthy cortical tissue.

7. The apparatus according to claim 6, wherein the path is designed to emit stimulation electrical signals at the edge of the damaged and/or partially damaged cortical tissue.

8. The apparatus according to claim 1, wherein the apparatus is configured to simultaneously stimulate selected pair of electrodes associated with specific pair of neural nodes.

9. The apparatus according to claim 1, wherein the processor is configured to compute the stimulation signals by using, a mathematical model of propagation of cortical waves.

10. The apparatus according to claim 1, wherein the processor is configured to apply the mathematical model of propagation of cortical waves, such that each stimulation signal is determined by a stimulation function $I(x,t)$, and
wherein the computer processor is configured to calculate numerically the stimulation function $I(x,t)$ applied to each electrode associated with the damaged and/or partially damaged cortical tissue and the healthy cortical tissue by numerically solving the equation:

$$I(x,t)=g(k-u)(H(W_a^{(1)}(u))-H(W_a^{(2)}(u)))-g(u)(H(W_i^{(1)}(u))-H(W_i^{(2)}(u)))$$

where K is a total neuron density, K-u is a density of not activated neurons, $W_a$ is an intensity of activating signal, $W_i$ is an intensity of inactivating signal, superscript (1) corresponds to the healthy tissue and superscript (2) to the damaged or partially damaged tissue, $g(u)$ and $H(W)$ are growing functions of the intensity of activating $(K-u)W_a$ represents a rate of neuron activation and $uW_i$ represents a rate of neuron inactivation.

11. The apparatus according to claim 10, wherein the processor is configured to apply external stimulation signal determined by the stimulation function $I(x,t)$ having the lowest value of the total stimulation=$\int_0^T \int_\Omega I^2(x,t)dxdt$.

12. The apparatus according to claim 10, wherein the processor is configured to apply external stimulation signal determined by the stimulation function $I(x,t)$ having the lowest value of maximal stimulation=max $I(x,t)$.

13. The apparatus according to claim 11 wherein the processor is configured to determine the value of external stimulation signal determined by the stimulation function $I(x,t)$, such that the process determines wave speed in the cortical tissue according to the formula $$c = \left(1 - \frac{2}{\sigma\gamma} + \frac{2l}{d\gamma}\right)$$

where σ characterizes cortical tissue excitability and γ characterizes cortical tissue connectivity.

14. The apparatus according to claim 11, wherein the stimulation signal determined by the stimulation function $I(x,t)$ is an increasing function of wave speed c in the cortical tissue.

15. The apparatus according to claim 11, wherein the processor is configured to determine whether the condition of

σγ>2 is satisfied in the cortical tissue,
where σ is a parameter characterizing cortical tissue excitability of healthy cortical tissue and γ is a parameter indicating cortical tissue connectivity.

16. A method for electrical brain stimulation comprising the steps of:
providing a plurality of electrodes;

generating electrical activity in a cortex of a person by using the plurality of electrodes, the cortex having pre identified crucial neural nodes associated with a selected brain function and including healthy cortical tissue and damaged and/or partially damaged cortical tissue, wherein the damaged cortical tissue includes damaged neural cells and the partially damaged cortical tissue includes partially damaged neural cells, the healthy, the damaged and/or partially damaged cortical tissue each having at least one parameter of cortical waves, wherein a value of the at least one parameter of the damaged and/or partially damaged cortical tissue is different from a value of the at least one parameter of the healthy cortical tissue, the at least one parameter being one of cortical wave propagation speed, amplitude and frequency;

emitting by the plurality of electrodes a stimulation electrical signals into the cortex and measuring electrical cortical waves;

emitting by the plurality of electrodes stimulation electrical signals in at least part of the healthy cortical tissue and the damaged and/or partially damaged cortical tissue, wherein at least some of the plurality of electrodes are positioned at areas corresponding to the pre-identified crucial neural nodes;

evaluating the at least one parameter of cortical waves between at least a first electrode and at least a second electrode corresponding respectively to a first pre-identified crucial neural node and a second pre-identified crucial neural node in the cortex based on the electrical cortical waves measured by the first electrode and second electrode between the first pre-identified crucial neural node and the second pre-identified crucial neural node, the first pre-identified crucial neural node and second pre-identified crucial neural node being situated such that a rectilinear line joining the first pre-identified crucial neural node and the second pre-identified crucial neural node crosses the damaged and/or partially damaged cortical tissue;

computing in real time, stimulation signals required to maintain the at least one parameter of cortical waves in a predetermined range between the first electrode and the second electrode and applying the computed stimulation signals to the plurality of electrodes.

17. The method according to claim 16, wherein the method is used to treat brain disorders during treatment of which traveling waves parameters are restored.

18. The method according to claim 16, where the method is used along with active participation of the patient during the external stimulation.

19. The method according to claim 16, wherein the applied computed stimulation signals are not applied to the plurality of electrodes continuously.

20. The method according to claim 19, wherein the applied computed stimulation signal is applied to the plurality of electrodes at discrete moments in time.

* * * * *